(12) United States Patent
Nowak et al.

(10) Patent No.: US 8,007,808 B2
(45) Date of Patent: Aug. 30, 2011

(54) COMPOSITION AND METHOD FOR FACILITATING THE INTERNALIZATION OF A THERAPEUTIC AGENT INTO A CELL

(75) Inventors: Romana A. Nowak, Urbana, IL (US); Robert J. Belton, Jr., Urbana, IL (US)

(73) Assignee: The Board of Trustees of the Univeristy of Illinois, Urbana, IL (US)

( * ) Notice: Subject to any disclaimer, the term of this patent is extended or adjusted under 35 U.S.C. 154(b) by 0 days.

(21) Appl. No.: 12/414,959

(22) Filed: Mar. 31, 2009

(65) Prior Publication Data

US 2010/0092494 A1 Apr. 15, 2010

Related U.S. Application Data

(60) Provisional application No. 61/042,505, filed on Apr. 4, 2008.

(51) Int. Cl.
- *A61K 38/00* (2006.01)
- *A61K 39/00* (2006.01)
- *A61K 39/38* (2006.01)
- *C07K 1/00* (2006.01)

(52) U.S. Cl. .................. 424/184.1; 424/185.1; 514/1.1; 530/350

(58) Field of Classification Search .................... None
See application file for complete search history.

(56) References Cited

U.S. PATENT DOCUMENTS

| | | | |
|---|---|---|---|
| 7,067,312 B1 * | 6/2006 | Bartel et al. | 435/325 |
| 2005/0214302 A1 * | 9/2005 | Nakada et al. | 424/155.1 |
| 2005/0221292 A1 * | 10/2005 | Kinoh et al. | 435/5 |

FOREIGN PATENT DOCUMENTS

WO WO 02/13763 * 2/2002

OTHER PUBLICATIONS

Zou et al (Zhongliu vol. 25, No. 1, pp. 46-50, 2005).*
Gabison et al., "EMMPRIN/CD147, an MMP modulator in cancer, development and tissue repair", Biochimie 2005 87:361-368.
Hanna et al., "A novel form of the membrane protein CD147 that contains an extra Ig-like domain and interacts homophilically", BMC Biochemistry 2003 4 (17) :1-9.
Miller et al., "Intercellular adhesion molecule-1 dimerization and its consequences for adhesion mediated by lymphocyte function associated-1", J. Exp. Med. 1995 182:1231-1241.
Sun et al., "Regulation of MMP-1 and MMP-2 production through CD147/extracellular matrix metalloproteinase inducer interactions", Cancer Research 2001 61:2276-2281.
Tang et al., "Extracellular matrix metalloproteinase inducer stimulates tumor angiogenesis by elevating vascular endothelial cell growth factor and matrix metalloproteinases", Cancer Research 2005 65 (8) :3193-3199.
Tomschy et al., "Homophilic adhesion of E-cadherin occurs by a co-operative two-step interaction of N-terminal domains", The EMBO Journal 1996 (15 (14) :3507-3514.
Xiong et al., "U-regulation of vascular endothelial growth factor in breast cancer cells by Heregulin-β1-activated p38 signaling pathway enhances endothelial cell migration", Cancer Research 2001 61:1727-1732.
Xu et al., "Leukocyte chemotactic activity of cyclophilin", Journal of Biological Chemistry 1992 267 (19) :11968-11971.
Yoshida et al., "Homo-oligomer formation by basigin, an immunoglobulin superfamily member, via its N-terminal immunoglobulin domain", Eur. J. Biochem. 2000 267:4372-4380.
Zhou et al., "Homophilic adhesion between Ig superfamily carcinoembryonic antigen molecules involves double reciprocal bonds", The Journal of Cell Biology 1993 122 (4) :951-960.

* cited by examiner

*Primary Examiner* — Albert Navarro
(74) *Attorney, Agent, or Firm* — Licata & Tyrrell P.C.

(57) ABSTRACT

The present invention is a composition and method for facilitating the internalization of a therapeutic agent into a cell. Specifically, the invention relates to the use of the extracellular domain of basigin-2, cyclophilin, or anti-basigin-2 antibody or antibody fragment as a delivery moiety for internalization of a therape.

2 Claims, 6 Drawing Sheets

```
         EXON 1          EXON 2
BSG1              MAAALFVLLGFALLGTHGASGA AGFVQAPLS QQRWVGGS
BSG2              MAAALFVLLGFALLGTHGASGA A--------  --------
BSG3              ---------------------  ---------  --------
BSG4  MKQSDASPQE- ---------------------  ---------  --------

EXON 3
BSG1  VELHCEAVGSPVPEIQWWFEGQGPNDTCSQLWDGARLDRVHIHATYHQHA
BSG2  -------------------------------------------------
BSG3  -------------------------------------------------
BSG4  -------------------------------------------------
        *

BSG1  ASTISIDTLVEEDTGTYECRAS NDPDRNHLTRAPRVKWVRAQAVVLVLE P
BSG2  ---------------------- ---------------------------
BSG3  ---------------------- ---------------------------
BSG4  ---------------------- ---------------------------
                  *
                          EXON 4
BSG1  GTVFTTVEDLGSKILLTCSL ND SATEVTGHRWLKGGVVLKEDALPGQKTE
BSG2  GTVFTTVEDLGSKILLTCSL ND SATEVTGHRWLKGGVVLKEDALPGQKTE
BSG3  --------------------------------------------------
BSG4  --------------------------------------------------
                          * N-GLY
         EXON 5                              EXON 6
BSG1  FK VDSDDQWGEYSCVFLPEPMGTANIQLH GP PRVKAVKSSEHINEGETAM
BSG2  FK VDSDDQWGEYSCVFLPEPMGTANIQLH GP PRVKAVKSSEHINEGETAM
BSG3  -- --------------MGTANIQLH     GP PRVKAVKSSEHINEGETAM
BSG4  -- VDSDDQWGEYSCVFLPEPMGTANIQLH GP PRVKAVKSSEHINEGETAM
                    *
                                          EXON 7
BSG1  LVCKSESVPPVTDWAWYKITDSEDK ALMNGSESRFFVSSSQGRSELHIEN
BSG2  LVCKSESVPPVTDWAWYKITDSEDK ALMNGSESRFFVSSSQGRSELHIEN
BSG3  LVCKSESVPPVTDWAWYKITDSEDK ALMNGSESRFFVSSSQGRSELHIEN
BSG4  LVCKSESVPPVTDWAWYKITDSEDK ALMNGSESRFFVSSSQGRSELHIEN
        *                           N-GLY

BSG1  LNMEADPGQYRCNGTSSKGSDQAIIT LRVRSHL AALWPFLGIVAEVLVLV
BSG2  LNMEADPGQYRCNGTSSKGSDQAIIT LRVRSHL AALWPFLGIVAEVLVLV
BSG3  LNMEADPGQYRCNGTSSKGSDQAIIT LRVRSHL AALWPFLGIVAEVLVLV
BSG4  LNMEADPGQYRCNGTSSKGSDQAIIT LRVRSHL AALWPFLGIVAEVLVLV
        *N-GLY
                        EXON 8       EXON 9
BSG1  TIIFIY EKRRKPEDVLD DDDAGSAPL KSSGQHQNDKGKNVRQRNSS
BSG2  TIIFIY EKRRKPEDVLD DDDAGSAPL KSSGQHQNDKGKNVRQRNSS
BSG3  TIIFIY EKRRKPEDVLD DDDAGSAPL KSSGQHQNDKGKNVRQRNSS
BSG4  TIIFIY EKRRKPEDVLD DDDAGSAPL KSSGQHQNDKGKNVRQRNSS
```

COMPOSITION AND METHOD FOR FACILITATING THE INTERNALIZATION OF A THERAPEUTIC AGENT INTO A CELL

This application claims benefit of priority from U.S. Provisional Patent Application Ser. No. 61/042,505 filed Apr. 4, 2008, the content of which is incorporated herein by reference in its entirety.

This invention was made with government support under U54 HD40093 awarded by the National Institutes of Health. The government has certain rights in the invention.

BACKGROUND OF THE INVENTION

The metastatic spread of cancer cells within host tissue is dependent upon the local microenvironment surrounding the primary tumor. Within this microenvironment, cancer cells stimulate surrounding stromal cells to express factors required for remodeling of the host tissue thus allowing for the survival, proliferation and metastasis of the tumor (Liotta & Kohn (2001) *Nature* 411(6835):375-379). Therefore, an understanding of the molecules mediating tumor-stromal cell interactions is critical for the development of strategies needed to diagnose and treat metastatic cancers. This need is underscored by the fact that many molecules identified as biological markers for metastatic cells are also expressed by host cells under normal physiological conditions (Gabison, et al. (2005) *Biochimie* 87(3-4):361-368). One particularly good example of such a molecule is the cell surface glycoprotein basigin. Basigin is an integral membrane glycoprotein belonging to the immunoglobulin superfamily (IGSF) and it is expressed on numerous cell types (Gabison, et al. (2005) supra; Yan, et al. (2005) *Thromb. Haemost.* 93(2):199-204; Muramatsu & Miyauchi (2003) *Histol. Histopathol.* 18(3): 981-987). Originally identified in LX-1 lung carcinoma cells as a secreted factor capable of stimulating the collagenase activity of human fibroblasts, basigin has been identified independently in several different model systems resulting in a long list of acronyms for this molecule including Tumor Collagenase Stimulatory Factor (TCSF) (Biswas (1982) *Biochem. Biophys. Res. Commun.* 109(3):1026-1034; Biswas (1984) *Cancer Lett.* 24(2):201-207; Nabeshima, et al. (1991) *Arch. Biochem. Biophys.* 285(1):90-96), EMMPRIN (Biswas, et al. (1995) *Cancer Res.* 55(2):434-439), neurothelin (Seulberger, et al. (1992) *Neurosci. Lett.* 140(1):93-97), OX-47 (Fossum, et al. (1991) *Eur. J. Immunol.* 21(3):671-679), gp42 (Altruda, et al. (1989) *Gene* 85(2):445-451), CE9 (Nehme, et al. (1993) *J. Cell Biol.* 120(3):687-694), 5A11 (Fadool & Linser (1993) *Dev. Dyn.* 196(4):252-262), HT7 (Seulberger, et al. (1990) *EMBO J.* 9(7):2151-2158), M6 (Kasinrerk, et al. (1992) *J. Immunol.* 149(3):847-854), OK blood antigen (Spring, et al. (1997) *Eur. J. Immunol.* 27(4): 891-897), and most recently CD147 ((1996) *Tissue Antigens* 48(4 Pt 2):352-508). Basigin is the approved HUGO Gene Nomenclature Committee designation for the human gene and will be used to refer to the gene sequence and the expressed proteins herein.

Human basigin has been shown to be expressed as two differentially spliced isoforms encoded by a single gene found on chromosome 19p13.3 (Kaname, et al. (1993) Cytogenet. Cell Genet. 64(3-4):195-197; Guo, et al. (1998) *Gene* 220(1-2):99-108; Hanna, et al. (2003) BMC Bioche. 4:17(18-20). The molecule is characterized by the presence of two extracellular immunoglobulin-like domains, a single transmembrane domain possessing a charged amino acid and a short cytoplasmic tail containing a basolateral membrane targeting motif (Miyauchi, et al. (1991) J. Biochem. (Tokyo) 110(5):770-774; Deora, et al. (2004) Mol. Biol. Cell 15(9): 4148-4165). The more recently identified retina-specific isoform of basigin is distinguished by an additional immunoglobulin-like sequence in the extracellular domain of the protein (Hanna, et al. (2003) supra; Ochrietor, et al. (2003) Invest. Opthalmol. Vis. Sci. 44(9):4086-4096). According to the current naming system of the National Center for Biotechnology Information, the larger retina-specific isoform has been renamed basigin-1 (GENBANK Accession No. NM_001728.2 and NP_001719.2) and the prototypical isoform, possessing two immunoglobulin domains, has been renamed basigin-2 (GENBANK Accession No. NM_198589.1 and NP_940991.1). Both basigin isoforms are variably glycosylated on asparagine residues, which results in significant alterations in their relative molecular weights depending upon the extent of $\beta 1,6$-branched polylactosamine incorporation during transit of the protein through the Golgi (Ochrietor, et al. (2003) supra; Tang, et al. (2004) Mol. Biol. Cell 15(9):4043-4050).

Several functions have been described for basigin within both normal and malignant tissues. The best characterized function for basigin is its ability to induce the expression of matrix metalloproteinases (MMPs) in stromal cells. Studies using tumor cell-stromal cell co-culture systems, or the treatment of stromal cells with soluble basigin protein demonstrated that basigin stimulates expression of several MMPs including MMP-1, -2, and -3 (Gabison, et al. (2005) supra). Evidence that cancer cells overexpress basigin and shed microvesicles containing basigin protein indicates that tumors can modify their local microenvironment by altering the balance between the expression level of MMPs and their physiological inhibitors, the Tissue Inhibitors of Matrix Metalloproteinases (TIMPs) (Sidhu, et al. (2004) *Oncogene* 23(4):956-963; Caudroy, et al. (2002) *Clin. Exp. Metastasis* 19(8):697-702). Despite a growing understanding of basigin function in tumor-stromal cell interactions, it has been unclear what protein on the surface of stromal cells functions as the receptor for basigin. Transfection of COS cells with a recombinant form of human basigin demonstrated that basigin can mediate cell adhesion events (Sun & Hemler (2001) *Cancer Res.* 61(5):2276-2281). Homophilic interactions have been demonstrated for other IGSF proteins including ICAMs (Miller, et al. (1995) *J. Exp. Med.* 182(5):1231-1241), NCAMs (Zhou, et al. (1993) *J. Cell Biol.* 122(4):951-960), and cadherins (Tomschy, et al. (1996) *EMBO J.* 15(14):3507-3514). However, attempts to demonstrate specific homophilic interactions between basigin molecules expressed on separate cells, or between soluble forms of recombinant basigin using surface plasmon resonance have not been successful (Hanna, et al. (2003) supra; Yoshida, et al. (2000) *Eur. J. Biochem.* 267(14):4372-4380).

Additional functions for basigin have been described. These include the ability of basigin to increase vascular endothelial growth factor (VEGF) production by tumor cells including breast cancer cells (Xiong, et al. (2001) *Cancer Research* 61:1727-32) as well as host fibroblast cells (Tang, et al. (2005) *Cancer Research* 65: 3193-9). Inhibition of basigin expression inhibits tumor growth in vivo while overexpression of basigin stimulates tumor angiogenesis. Thus, basigin plays an important role in regulating angiogenesis.

SUMMARY OF THE INVENTION

The present invention is a composition for facilitating the internalization of a therapeutic agent into a cell. The composition is composed of a delivery moiety operably linked to a therapeutic agent, wherein the delivery moiety is selected from the group of the extracellular domain of basigin-2, anti-basigin-2 antibody or antibody fragment, and cyclophilin. Methods for using this composition to facilitate the internalization of a therapeutic agent into a cell and kill a cancer cell are also provided, as are vectors and host cells harboring a nucleic acid molecule encoding basigin-2.

BRIEF DESCRIPTION OF THE DRAWINGS

FIG. 5 depicts an amino acid sequence alignment of the basigin isoforms. The conceptually translated cDNA sequences for basigin-1 (SEQ ID NO:9), -2 (SEQ ID NO:10), -3 (SEQ ID NO:11) and -4 (SEQ ID NO:12) were aligned using the Biology Workbench program ClustalW. The exon boundaries are indicated and separated by vertical lines. The signal peptide sequence in exon 2 is shown in bold letters. The Ig-like domains are indicated with boxes. The transmembrane domain in exon 7 is indicated with a box having a dashed line. The single lysine residue that functions as a basolateral targeting motif is found in exon 9 (bold 'k'). The tenth exon is not translated. Asparagine glycosylation sites are indicated by bold letters and underscored with 'N-Gly'. The conserved cysteine residues necessary for stabilization of the immunoglobulin folds are indicated by asterisks.

FIG. 6 shows that basigin-2 is a membrane receptor for rBSG. In FIG. 6A, 20 µg of unlabeled HESC membrane (Mem) and cytosolic (Cyto) protein was resolved by SDS-PAGE and immunoblotted for the membrane protein caveolin-1, basigin, and the cytoplasmic protein SOS. Insufficient amounts of basigin-3 are present within 20 µg of each fraction to be detected.

FIG. 7 shows reciprocal basigin-neutravidin precipitations which confirm that rBSG interacts with basigin-2 and basigin-3. Biotin label transfer from rBSG to CCL-2 cells (HeLa) was performed by treating cells with increasing concentrations of SEED-labeled rBSG (0, 0.05, 0.5, 5, and 50 µg/ml) for 10 minutes at 37° C. Following 5 minutes of UV light treatment, cells were washed twice with PBS and total cell lysates collected using IP buffer. Proteins from labeled cells were precipitated with either neutravidin beads (FIGS. 7A and 7B) or immunoprecipitated with the P2C2 mAb (FIGS. 7C and 7D). Precipitated proteins were resolved by 15% SDS-PAGE in duplicate, and immunoblotted with either Streptavidin-HRP (FIGS. 7A and 7C) or with the R&D Systems anti-hEMMPRIN pAb (FIGS. 7B and 7D). The Santa Cruz goat anti-rabbit (anti-mouse, anti-human depleted)-HRP secondary antibody used for this experiment was previously shown to not cross-react with the P2C2 mAb. The basigin-2 band is indicated with an arrowhead and the basigin-3/rBSG band is indicated with an arrow. This experiment was performed twice with similar results.

DETAILED DESCRIPTION OF THE INVENTION

Figure 1:
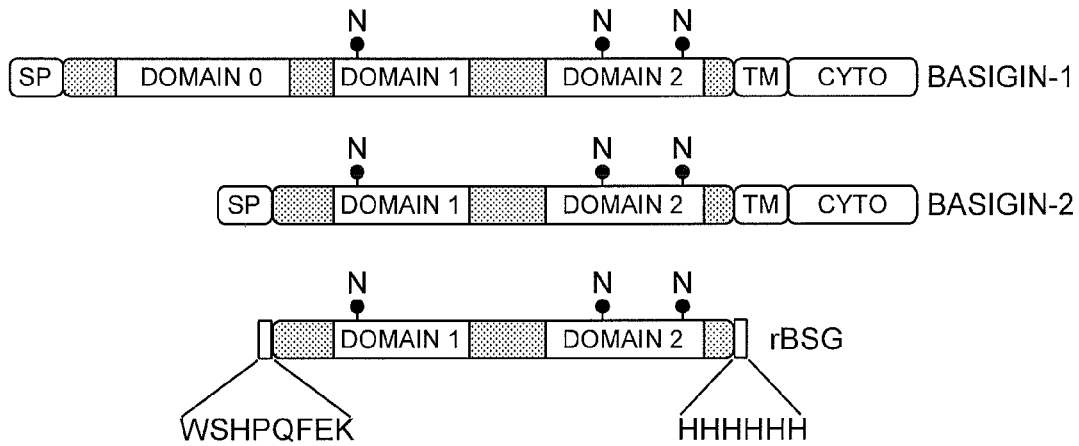
FIG. 1 depicts a comparison of the recombinant human basigin extracellular domain construct (rBSG) to full-length human basigin-1 and basigin-2. N=consensus asparagine-linked glycosylation sites, SP=signal peptide sequence, TM=transmembrane domain, Cyto=cytoplasmic domain. The amino-terminal StrepTag II sequence, Trp-Ser-His-Pro-Gln-Phe-Glu-Lys (SEQ ID NO:1), and the carboxyl-terminal 6×His sequence (SEQ ID NO:2) of rBSG are shown.

It has now been demonstrated that the extracellular domain of basigin-2 possesses a stable folded structure in solution. This novel non-glycosylated recombinant basigin-2 protein (rBSG) activates the ERK1/2 signaling pathway; stimulates the expression of MMP-1, MMP-2, and MMP-3 in a dose-dependent manner; and facilitated the identification of receptors for the soluble basigin ligand. The ability of a non-glycosylated form of basigin to induce MMP expression in fibroblasts was unexpected and contradicts previous studies indicating that N-glycosylation of basigin is necessary for its stimulatory activity (Sun & Hemler (2001) *Cancer Res.* 61(5):2276-2281; Guo, et al. (1997) *J. Biol. Chem.* 272(1): 24-27). Moreover, basigin-2 has now been shown to be a receptor for itself such that secreted/soluble basigin-2 can bind to the transmembrane form of basigin-2 to activate signaling. In addition, once soluble basigin-2 binds to the basigin-2 receptor in the membrane, the whole complex is internalized into the cell. This internalization of the ligand-receptor complex now provides a novel drug therapy approach, wherein basigin-2 protein, an antibody to basigin-2, or cyclophilin (also known to bind basigin-2), or any other soluble ligand that can bind to basigin isoform-2 in the cell membrane, is operably linked to a therapeutic agent (e.g., a toxin such as saporin or maytansinoids), wherein upon binding to the basigin-2 receptor, the entire complex is internalized into the cell where the therapeutic agent can exert its activity. In this regard, a cyclophilin, a rBSG protein or an antibody thereto can deliver the therapeutic agent as a prodrug. Accordingly, the present invention embraces a construct composed of a delivery moiety operably linked to a therapeutic agent for use in delivering the therapeutic agent into a cell, wherein the delivery moiety is selected from the group of cyclophilins, a recombinant or native rBSG protein, an anti-basigin-2 antibody or antibody fragment, or any other protein ligand that can bind to basigin-2 expressed in the cell membrane of target cells.

For the purposes of the present invention, a recombinant basigin-2 protein can be the full length basigin-2 protein or more desirably is a fragment of the basigin-2 protein encompassing the extracellular domain of basigin-2, specifically amino acids 23-206 of the basigin-2 protein set forth in SEQ ID NO:10. In this regard, the basigin-2 protein of the invention is approximately 150 to 260 amino acid residues in length, 160 to 240 amino acid residues in length, 170 to 220 amino acid residues in length, or 180 to 200 amino acid residues in length. In particular embodiments, the basigin-2 protein of the invention is or contains the extracellular domain set forth in SEQ ID NO:13.

In addition to the human basigin-2 protein disclosed herein, it is contemplated that a basigin-2 protein isolated from other species can also be used to facilitate transport of molecules into cells. A basigin-2 protein from another species can be identified by hybridizing a nucleic acid molecule encoding human basigin-2 protein under stringent hybridization conditions to DNA isolated from the species of interest. Stringent hybridization conditions are well-known in the art and generally include hybridization at 7% sodium dodecyl sulfate (SDS), 0.5 M $NaPO_4$ pH 7.0, 1 mM EDTA at 50° C. followed by one or more washes with 2×SSC, 1% SDS, at 50° C. See, e.g., Sambrook et al., *Molecular Cloning, A Laboratory Manual* (2d Ed. 1989) (Cold Spring Harbor Laboratory). Alternatively, a basigin-2 protein from another species can be identified by sequence comparisons using conventional algorithms such as BLAST or BLASTP.

Nucleic acids encoding the rBSG protein can be obtained from any suitable source by conventional methods such as restriction endonuclease cleavage of genomic DNA or PCR amplification as disclosed herein. In particular embodiments, the nucleic acid encoding the rBSG protein includes exons 4, 5, 6 and 7. For recombinant protein expression of the rBSG protein, nucleic acids are typically cloned into an expression vector and the recombinant protein is expressed and purified. Any suitable expression system can be employed including bacterial (e.g., *E. coli*), fungal (e.g., yeast), insect, or mammalian expression systems. Suitable expression vectors and cells are well-known to those skilled in the art and obtained from commercial sources such as STRATAGENE and CLONTECH.

In so far as rBSG finds application in therapeutic approaches as well as in basic research for screening and analyzing the effects of novel therapeutics (e.g., siRNA), particular embodiments of this invention embrace an expression vector harboring a nucleic acid encoding at least a portion of the full-length basigin-2 protein, host cells harboring said vector and a kit containing the same. In particular embodiments, the portion of basigin-2 encoded by the nucleic acids is 170 to 220, or 180 to 200 amino acid residues in length and encodes the extracellular domain of basigin-2.

To facilitate expression and purification, the rBSG protein can be also contain one or more tags or a signal sequence for secretion of rBSG into the culture medium. Tags typically employed in the art include biotin, His6, c-myc, FLAG, and the like, which can be used to affinity-purify rBSG. For expression in prokaryotes, particular embodiments also embrace a rBSG protein with a signal sequence, which directs the expressed rBSG protein to the periplasmic space thereby exposing the rBSG protein to an oxidative environment allowing for the formation of intra-molecular disulfide bonds during translocation into the periplasm (Nakamoto & Bardwell (2004) *Biochim. Biophys. Acta* 1694(1-3):111-119). Such sequences include, e.g., the StrepTag II sequence set forth herein in SEQ ID NO:1.

In addition to rBSG protein, the present invention also embraces an rBSG antibody or antibody fragment as a delivery moiety for delivering a therapeutic agent into a cell. Antibodies of use in accordance with the present invention can be monoclonal or polyclonal. It is contemplated that such antibodies can be natural or partially or wholly synthetically produced. All fragments or derivatives thereof which maintain the ability to specifically bind to and recognize the BSG are also contemplated. In particular embodiments, the antibody or antibody fragment binds to and recognizes the extracellular domain of basigin-2 disclosed herein. The antibodies can be a member of any immunoglobulin class, including any of the classes: IgG, IgM, IgA, IgD, and IgE. Derivatives of the IgG class, however, are preferred in the present invention.

Antibody fragments can be any derivative of an antibody which is less than full-length. Preferably, the antibody fragment retains at least a significant portion of the full-length antibody's specific binding ability. Examples of antibody fragments include, but are not limited to, Fab, Fab', F(ab')$_2$, scFv, Fv, dsFv diabody, or Fd fragments. The antibody fragment may be produced by any means. For instance, the antibody fragment may be enzymatically or chemically produced by fragmentation of an intact antibody or it may be recombinantly produced from a gene encoding the partial antibody sequence. The antibody fragment may optionally be a single-chain antibody fragment. Alternatively, the fragment may comprise multiple chains which are linked together, for instance, by disulfide linkages. The fragment may also optionally be a multi-molecular complex. A functional antibody fragment will typically comprise at least about 50 amino acids and more typically will comprise at least about 200 amino acids. As used herein, an antibody also includes bispecific and chimeric antibodies.

Naturally produced antibodies are generated using well-known methods (see, e.g., Kohler and Milstein (1975) *Nature* 256:495-497; Harlow and Lane (1988) supra). Alternatively, antibodies are derived by a phage display method. Methods of producing phage display antibodies are well-known in the art (e.g., Huse, et al. (1989) *Science* 246(4935):1275-81). As with the rBSG protein, the anti-BSG antibody or antibody fragment can be tagged, contain a signal sequence, and/or expressed by a host cell harboring an expression vector capable of expressing the anti-BSG antibody or antibody fragment. Moreover, the host cell and/or vector can be provided in a kit.

In addition to its role in cancer and angiogenesis, basigin is also known to bind with cyclophilins. Cyclophilins are secreted proteins that are known to act as chemotactic factors for various subsets of leukocytes. The chemotactic capacity of cyclophilins is dependent on interaction between extracellular cyclophilins and the cell membrane form of basigin, basigin isoform-2. This interaction leads to an activation of cell signaling in leukocytes including T cells and neutrophils (Xu, et al. (1992) *J. Biol. Chem.* 267:11968-11971) and will ultimately lead to their activation and recruitment into tissues during inflammatory processes. This has in fact been shown to be the case in asthma-induced lung inflammation (Gwinn, et al. (2006) *J. Immunology* 177:4870-9). Accordingly, in so far as cyclophilins bind the cell membrane form of basigin-2, another embodiment of the invention features cyclophilin as a delivery moiety to facilitate the internalization of therapeutic agents linked thereto. Accordingly, certain embodiments of the present invention embrace replacing rBSG with a cyclophilin. Cyclophilins of use in this invention are well-known in the art and include, but are not limited to those set forth in GENBANK Accession No. NP_066953. As with the rBSG protein, the cyclophilin can be tagged, contain a signal sequence, and/or expressed by a host cell harboring an expression vector capable of expressing the cyclophilin. Moreover, the host cell and/or vector can be provided in a kit.

In accordance with the present invention, a therapeutic agent is operably linked to the delivery moiety so that the therapeutic agent is delivered via the delivery moiety into the cytoplasm of the cell. A therapeutic agent can be operably linked to the delivery moiety by covalent or non-covalent bonds. In addition, the linkage can be indirect or direct. Wherein the therapeutic agent is a protein, e.g., an antibody, antibody fragment, peptide hormone, and the like, the therapeutic agent can be expressed in-frame with the delivery moiety. Wherein the therapeutic agent is a small organic molecule (e.g., saporin) or nucleic acid (e.g., siRNA), the therapeutic agent can be directly linked to the delivery moiety via the N-terminus, C-terminus, or reactive side chains (e.g., Lys or Cys) of the delivery moiety. Such linkages are routinely carried out in the art by, e.g., maleide-activation. As demonstrated herein using the Streptavidin-ZAP system, the therapeutic agent can also be indirectly linked to the delivery moiety. Such indirect linkages can be via ligand-receptor binding partners (e.g., biotin-streptavidin) or antigen-antibody binding partners, wherein one of the binding partners is linked to the delivery moiety and the other binding partner is linked to the therapeutic agent. As such, when the binding partners interact, the therapeutic agent is indirectly linked to the delivery moiety.

Therapeutic agents particularly embraced by the present invention include, but are not limited to, anti-inflammatory agents, anti-cancer agents (e.g., cytotoxic agents), anti-infectives (e.g., anti-virals, anti-parasitics, anti-bacterials and anti-mycotics), and endocrine and metabolic drugs (e.g., steroids, peptides and peptide hormones). Classes of compounds specifically embraced by the present invention include, a mitotoxin, a chemotherapy drug, a siRNA, or an apoptosis-inducing molecule. In this regard, cells being targeted include, but are not limited to, cancer cells; inflammatory cells; and cells infected with a parasite, virus, bacterium, or fungus.

According to particular embodiments of this invention, the therapeutic agent is a cytotoxic agent (e.g., saporin) which kills cancer cells. Thus, the present invention features a method for killing a cancer cell, in particular a cancer cell expressing the basigin-2 receptor on its cell surface. The method involves contacting the cancer cell with a delivery moiety disclosed herein operably linked to a cytotoxic agent so that the cytotoxic agent is internalized and the cancer cell is killed. In some embodiments, this method is carried out in vivo. In other embodiments, this method is carried out in vitro.

In so far as the rBSG protein is functional and can induce the expression of multiple MMPs (i.e., MMP-1, MMP-2 and MMP-3), particular embodiments embrace operably linking the delivery moiety to the therapeutic agent via an MMP cleavage sequence. In this regard, the therapeutic agent is specifically released only in cells which express BSG on the cell surface (i.e., available for binding rBSG or anti-BSG antibody), thereby facilitating accumulation of the therapeutic agent in the target cells. This is particularly advantageous when the therapeutic agent is a toxic compound to be delivered to, e.g., a cancer cell. By delivering the toxic compound as a prodrug via a delivery moiety, non-target cells are protected from the toxic effects of the toxic compound. Suitable MMP cleavage sequences are known in the art and a comprehensive list of MMPs and their cognate cleavage sequences is available from the MEROPS database (see Rawlings, et al. (2002) *Nucl. Acids Res.* 30:343-346).

Specific delivery of a therapeutic agent into a cell can be used in the treatment of a variety of diseases including, but not limited to cancer, inflammatory disorders, and the like. In particular, there are a number of diseases or conditions for which MMPs have an associated role, e.g., cancer (including breast cancer, colorectal cancer, renal cell carcinoma, malignant melanoma, endometriosis, cervical cancer, and bladder cancer), osteoarthritis, ulcerative colitis, early implant failure, inflammatory bowel disease, delayed wound healing, progressive adult-onset emphysema, and heart failure. As such, an rBSG protein linked to the therapeutic agent via an MMP cleavage sequence finds particular application in the treatment of these MMP associated diseases and conditions.

Moreover, because of the interaction between basigin and cyclophilins and the resultant activation of inflammatory processes, it is expected that replacing the rBSG component of the instant composition with cyclophilin will be particularly useful in the treatment of inflammatory type diseases. Indeed, there are several reports of increased cell surface basigin expression in synoviocytes and monocytes in rheumatoid arthritis (Zhu, et al. (2006) *Arthritis Res. Therap.* 8:R44; and Zhu, et al. (2005) *Arthritis Res. Therap.* 7:R1023-33). Basigin expression is also elevated in various cardiac pathologies including increased expression in the myocardium of patients with cardiomyopathy (Spinale, et al (2000) *Circulation* 102: 1944-1949), increased expression in the myocardium of patients with aortic stenosis (Fielitz, et al. (2004) *J. Molec. Medicine* 82:809-820), increased expression after myocardial ischemic injury (Yamani, et al. (2002) *Circulation* 105: 1955-61); and increased expression in monocytes in the myocardium during myocardial infarction (Schmidt, et al. (2006) *Circulation* 113:834-841).

Accordingly, other diseases that may be targeted with this invention are chronic inflammatory diseases such as Crohn's disease and lupus; dermatological diseases such as scleroderma, psoriasis, telangiectasis, dermatitis, venous ulcers, acne, and hemangiomas which are angiogenesis-dependent; and opthalmological diseases such as diabetic retinopathy and macular degeneration.

For therapeutic applications, the composition of the invention can be formulated in a pharmaceutical composition, wherein the therapeutic agent operably linked to the delivery moiety is in admixture with a pharmaceutically acceptable carrier. Such pharmaceutical compositions can be prepared by methods and contain carriers which are well-known in the art. A generally recognized compendium of such methods and ingredients is Remington: The Science and Practice of Pharmacy, Alfonso R. Gennaro, editor, 20th ed. Lippincott Williams & Wilkins: Philadelphia, Pa., 2000. A pharmaceutically acceptable carrier, or vehicle, such as a filler, diluent, excipient, or solvent encapsulating material, is involved in carrying or transporting the subject compound from one organ, or portion of the body, to another organ, or portion of the body. Each carrier must be acceptable in the sense of being compatible with the other ingredients of the formulation and not injurious to the subject being treated. The carrier can be a solid or a liquid, or both, and is can be formulated with the active ingredient as a unit-dose formulation, for example, a tablet, which can contain from 0.01 or 0.5% to 95% or 99% by weight of the active ingredient.

The carrier selected may be dependent upon the route of administration (e.g., topical, oral, parenteral, and the like). Examples of materials which can serve as carriers include sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in formulations. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

The invention is described in greater detail by the following non-limiting examples.

Example 1

Materials and Methods

Cell Lines and Reagents. Immortalized human endometrial stromal cells (HESC) are known in the art and were cultured according to known methods (Krikun, et al. (2004) *Endocrinology* 145(5):2291-2296). The human cervical carcinoma cell lines CCL-2 (HeLa), C4-I, and C4-II were purchased from American Type Culture Collection (Manassas, Va.) and cultured using the protocols provided. The P2C2 basigin monoclonal antibody was generated according to standard methods. The pASK_IBA44 bacterial expression vector was from IBA (Göttingen, Germany). Custom oligonucleotide primers were purchased from Integrated DNA Technologies, Inc. (Coralville, Iowa). The ERK1/2 antibodies and Hrp-conjugated secondary antibodies were from Cell Signaling (Beverly, Mass.). Restriction endonucleases, phosphatase, and ligase reagents were from New England Biolabs (Ipswich, Mass.). The anti-rabbit Hrp-conjugated secondary antibody (anti-human, anti-mouse depleted) was from Santa Cruz Laboratories (Santa Cruz, Calif.). The anti-human EMMPRIN polyclonal antibody (pAb) was from R&D technologies. PFU ultra polymerase and BL21-RP Codon-plus *E. coli* were from STRATAGENE (La Jolla, Calif.). The caveolin-1, SOS and HIM6 antibodies and SUPERSCRIPT III reverse transcriptase were from INVITROGEN (Carlsbad, Calif.). The Sulfo-SBED biotin label transfer kit, D-SALT dextran columns, NEUTRAVIDIN ULTRALINK and protein G beads, and Pico chemiluminescent detection reagent were from Pierce Biotechnology (Rockford, Ill.). PRIMESTAR HS polymerase was from Takara Mirus (Shiga, Japan). TAQMAN universal PCR Master Mix, 20× Assays and MICROAMP optical 384-well reaction plates were from Applied Biosystems (Foster City, Calif.).

Generation and Purification of rBSG. The extracellular domain of human basigin, corresponding to amino acids 23-206 of isoform 2, was amplified by high-fidelity PCR amplification using ORF Forward and ORF Reverse primers (see Table 1). The resulting PCR product was ligated into the BsaI-linearized pASK_IBA44 vector and the DNA sequence of the construct was determined.

TABLE 1

| Primer | Sequence (5'->3') | SEQ ID NO: |
|---|---|---|
| ORF | ATGGTAGGTCTCAGCGCCGCCGGCACAGTCTTCACTAC | 14 |
| Forward c | | 15 |
| ORF | ATGGTAGGTCTCAGGCCCAGGTGGCTGCGCACGCGG | 16 |
| Reverse | CGGCTTAGTCTGCGGTCC | 17 |
| Primer a | CCGGTTGGAGGTTGTAGGAC | 18 |
| Primer e | TCCGACTGCTTCATTGTGGG | 19 |
| Primer f | GGGAGGAAGACGCAGGAGTA | 20 |
| Primer g | TTTTTTGAGGGTGGAGGTGG | |
| Primer h | | |

For recombinant protein expression, the IBA44-rBSG construct was transformed into the BL21-RP CODONPLUS strain of *E. coli*. Single bacterial colonies were inoculated into SOC media containing ampicillin and chloramphenicol (SOC/A/C). Cultures were grown for 6 hours at 37° C., 250 RPM, diluted 1/100 into SOC/A/C and grown for 12-14 hours at 25° C., 250 RPM. Cultures were diluted 1/5 into SOC/A, grown until the $OD_{550}$>0.8 and protein expression induced with the addition of 0.2 mg/ml anhydrotetracycline (AHT). Following 6 hours induction, detergent-free osmotic shock lysate (OSL) was generated according to standard methods. Briefly, bacteria were resuspended in 80 ml per gram-wet weight of ice-cold sucrose buffer (20% sucrose, 30 mM Tris pH 8), 1 mM EDTA was added drop-wise, and the cells incubated on ice for 10 minutes. Cells were collected by centrifugation at 8000×g 20 minutes at 4° C., the sucrose buffer discarded, and the bacteria resuspended in 5 mM $MgSO_4$. Following centrifugation at 8000×g for 20 minutes, the OSL was filtered through a 0.22 mm cellulose acetate filter to remove cellular debris, concentrated 250-fold using 10 kDa centrifugal filters, and dialyzed into wash buffer (300 mM NaCl, 50 mM $NaH_2PO_4$ pH 8). The OSL from 1 liter of culture was incubated with 1 ml of TALON Metal Affinity Beads (Amersham, Piscataway, N.J.) for 90 minutes at 4° C. The bound protein was washed with >30 bed volumes of wash buffer, followed by 10 bed volumes of wash buffer containing 5 mM imidazole. The recombinant protein was eluted with 10 bed volumes of wash buffer containing 200 mM imidazole. The eluted protein was dialyzed into phosphate-buffered saline and characterized by SDS-PAGE, PFO-PAGE and immunoblot analysis.

PFO-Page. rBSG protein was analyzed by perfluorooctanoate polyacrylamide gel electrophoresis (PFO-PAGE) according to established methods (Ramjeesingh, et al. (1999) Biochem. J. 342 (Pt 1):119-123). The purified rBSG protein was diluted into PFO-PAGE sample buffer (50 mM Tris pH 8, 10% glycerol, 4% PFO) and loaded onto an 8% native polyacrylamide gel that had been pre-run for 45 minutes at 50 volts in PFO running buffer (25 mM Tris pH 8, 192 mM glycine, 0.5% PFO).

Endotoxin Analysis of rBSG. Measurement of bacterial endotoxin present in the purified rBSG was performed by Cambrex Bioscience Walkersville, Inc (Walkersville, Md.) using the Limulus Amoebocyte Lysate (LAL) assay. One hundred mg/ml of rBSG was analyzed following established FDA guidelines (SOP 162.6).

Quantitative Real Time PCR Analysis. HESCs grown to 90% confluency in 10 cm dishes were treated with rBSG at 0.1, 1, 10, and 100 mg/ml for 24 hours in serum-free DMEM/F12 at 37° C. Total RNA was isolated using the TRIZOL method, reversed-transcribed into cDNA, and analyzed by Real-time PCR using TAQMAN Universal PCR Master Mix. MMP-1, MMP-2, MMP-3, and GAPDH sequences were amplified using the 20× ASSAYS-ON-DEMAND Gene Expression Assay. Real-time PCR amplification and detection was performed in MICROAMP optical 384-well reaction plates using the ABI 7900 sequence detection system. Relative fold differences between the tested genes were obtained by the comparative Ct method. To show changes in gene expression relative to control level (control set as 1), each biological replicate was normalized to the average of the control group within each experiment. Relative fold difference values for each experiment were checked for normality and common variances, respecting the assumptions for performing analysis of variance. All distributions were normal, and experiments with unequal variances were analyzed by Welch's ANOVA. A completely randomized design corresponding to the following linear model was used: $Xij=\mu+\tau i+\epsilon ij$, where $Xij$: an observation, $\mu$: population mean, $\tau i$: effect of ith treatment, $\epsilon ij$: error term. Post Hoc comparisons using Tukey's procedure ($\alpha=0.05$) were only performed when ANOVA indicated significant effect due to treatment. The data analysis for this paper was generated using SAS software (Copyright, SAS Institute Inc.).

Collection of Cell Lysates and Cell Fractions. Soluble cell lysates were collected in ice-cold immunoprecipitation buffer (IP buffer: 1% NONIDET P-40, 0.5% Deoxycholate, 0.1% SDS, 20 mM HEPES pH 7.4, 150 mM NaCl, 1 mM EDTA, 1 mM $Na_3VO_4$, 1 mM NaF, 10% glycerol, 0.5 mM PMSF, protease inhibitors). Lysates were incubated on ice for 30 minutes, centrifuged at 20,000×g for 15 minutes 4° C., and the soluble fraction collected. For cell fractionation studies, cells were harvested by scraping cells into ice-cold hypoosmotic buffer (10 mM Tris pH 7.4, 2 mM EDTA, protease inhibitor cocktail), sonicated for 5 seconds, and spun at 500×g for 10 minutes at 4° C. to remove nuclei and cell debris. The supernatant was transferred to a BECKMAN SW-55Ti rotor and centrifuged at 100,000×g for 15 minutes 4° C. The soluble cytoplasmic fraction was collected and the remaining membrane pellet was solubilized in IP buffer. Protein concentration determination was performed using the BCA method.

Immunoprecipitation and Immunoblot Analysis. Immunoprecipitation of basigin was performed using the monoclonal antibody P2C2. Ten to 15 mg of antibody added to 1 mg soluble protein was incubated overnight at 4° C. with rocking, and immune complexes were collected on protein G SEPHAROSE beads for 4 hours at 4° C. Immunoprecipitated proteins were resolved by SDS-PAGE using standard methods. For immunoblotting, SDS-PAGE gels were transferred to nitrocellulose, blocked in TBST (20 mM Tris pH8, 150 mM NaCl, 0.1% TWEEN-20) containing 5% non-fat dry milk for 60 minutes at room temperature, and incubated with primary antibodies as indicated. Hrp-conjugated secondary antibodies were used at a dilution of 1:15,000. The blots were washed and the bands visualized using the Pierce Pico chemiluminescence reagent.

siRNA Knockdown of Basigin. Basigin protein expression was knocked down by reverse transfection using the basigin SILENCER small interfering RNA oligonucleotide and the SIPORT Amine transfection reagent according to the manufacturers recommendations (Ambion, Austin, Tex.). Proliferating HESCs were harvested and 80,000 cells plated in 12-well dishes containing 60 nM oligonucleotide. Control transfections used the SILENCER Negative Control #1 siRNA. Media was replaced 48 hours post-transfection and cells treated with 10 mg/ml rBSG or 100 ng/ml recombinant human EGF for the times indicated. Cell lysates were collected by addition of 100 ml boiling 2% SDS, 62 mM Tris pH 6.8, 10% glycerol.

Biotin Label Transfer and Protein Purification. Purified rBSG was labeled with the heterotrifunctional crosslinking reagent Sulfo-SBED according to the manufacturers recommendations. For this, rBSG protein was combined with the Sulfo-SBED Label Transfer reagent at a molar ration of 1:4 in the dark at 4° C. for 2 hours. Unincorporated Sulfo-SBED was removed by gel filtration on D-SALT dextran desalting columns. Labeled rBSG was diluted into pre-warmed, serum-free culture medium and added to the cells. Cells were incubated with the labeled protein at 37° C. in the dark for 10 minutes and crosslinked using a STRATALINKER UV light source for 5 minutes. The medium was aspirated and the HESCs washed twice with PBS. Soluble cell lysate from $5(10)^7$ cells was prepared and applied to a 1 ml bed of Monomeric Avidin ULTRALINK beads (Pierce) for 1 hour at 4° C., and the column washed with 20 volumes of column buffer (1×PBS pH 7.4, 1 mM EDTA, 0.05% TWEEN-20). The rBSG ligand was eluted from the column with 5 bed volumes of column buffer containing 50 mM DTT. All remaining biotinylated proteins were eluted with 5 bed volumes of 2 mM D-Biotin in column buffer followed by 5 bed volumes of 100 mM glycine pH 3.0. The glycine sample was neutralized with 1 M Tris pH 9.5 and all fractions were concentrated and dialyzed into phosphate-buffered saline (PBS) using 10,000 molecular weight cut off (MWCO) centrifugal filters. Eluted proteins were resolved by 15% Precast Tris-glycine SDS-PAGE (BIO-RAD, Hercules, Calif.) and either immunoblotted with Streptavidin-Hrp or stained in 0.1% COOMASSIE Brilliant Blue. For protein sequencing, purified biotinylated proteins were excised from COOMASSIE-stained SDS-PAGE gels and identified by MALDI tandem mass spectrophotometry using an Applied Biosystem 4700 TOF/TOF. The identities of the peptide sequences were determined by comparison to the non-redundant NCBI database using the MASCOT search engine.

Cloning and Sequencing Analysis of Basigin Isoforms 3 and 4. The nucleotide sequences corresponding to the sequenced peptides were used to map the exon-intron boundaries between the basigin isoforms using SPIDEY. Oligonucleotide primers complimentary to exons 1, 2, 5 and 10 of human basigin were generated (Table 1). Total RNA was isolated from HESC, CCL-2, C4-I, and C4-II cells, and oligo dT or random decamer-primed cDNA was generated using the SUPERSCRIPT III reverse transcriptase. cDNA sequences were amplified using PRIMESTAR HS polymerase, subcloned into the PBLUESCRIPT II KS (−) plasmid vector and sequenced.

Example 2

Identification of Novel Basigin Isoforms

The extracellular domain of basigin-2 was expressed periplasmically in E. coli as a polyhistidine-tagged fusion protein (FIG. 1). Periplasmic expression exposes recombinant proteins to an oxidizing environment during the translocation through the periplasm resulting in the formation of intramolecular disulfide bonds (Nakamoto & Bardwell (2004) Biochim. Biophys. Acta 1694(1-3):111-119). The conserved cysteine residues flanking the immunoglobulin folds of basigin were anticipated to form disulfide bonds stabilizing the folded, native protein. To determine whether recombinant basigin (rBSG) possessed tertiary structure, rBSG was subjected to non-reducing and reducing SDS-PAGE. The results indicate that the periplasmically expressed rBSG migrates at a reduced molecular weight in a non-reducing SDS-PAGE (21 vs. 23 kDa), demonstrating that the protein possesses a stable tertiary structure. Basigin is known to multimerize within the plasma membrane of cells, and this interaction is mediated in part by the first immunoglobulin domain (Yoshida, et al. (2000) supra). To determine whether rBSG could form multimers in solution, PFO-PAGE was performed. The use of the detergent perfluorooctanoate in place of SDS during polyacrylamide gel electrophoresis allows for the maintenance of weak protein-protein interactions. Immunoblot analysis of rBSG protein resolved by PFO-PAGE demonstrated that rBSG forms dimers in solution only when the immunoglobulin domains of the protein are maintained in their non-reduced, native conformation.

Figure 2:
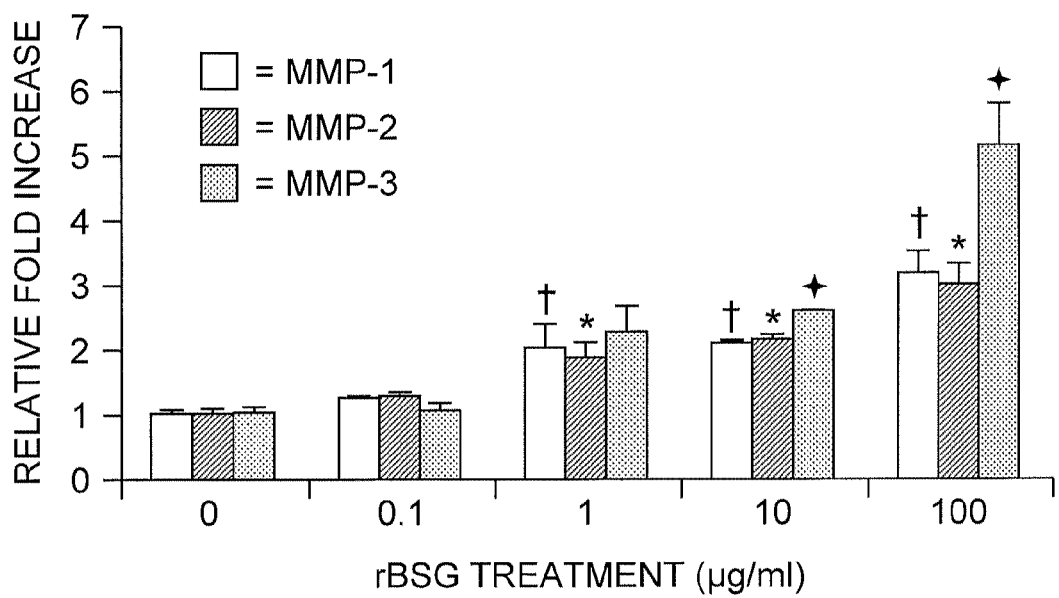
FIG. 2 is a graph showing that rBSG stimulates MMP expression in HESC cells. HESC cells were treated with the indicated concentrations of rBSG for 24 hours and the fold change in the expression of MMPs determined by quantitative real-time PCR. Results from three independent experiments are shown. Error bars represent standard error. Analysis of variance was performed using Welch's ANOVA and the statistical significance of the fold change was determined using Tukey's procedure ($\alpha$<0.05). Significant gene expression changes over controls are indicated by symbols: † (MMP-1), * (MMP-2) or ✦(MMP-3).

The evidence that rBSG maintains a native conformation in solution indicated that the protein might function as a ligand to stimulate matrix metalloproteinase (MMP) expression in fibroblasts. To test this, human uterine fibroblasts (HESCs) (Krikun, et al. (2004) supra) were treated with rBSG for 24 hours and the expression of MMP-1, -2 and -3 was determined using quantitative real-time PCR. rBSG stimulated a dose-dependent increase for each MMP with the increases in MMP-1 and MMP-2 expression being statistically significant at 1 mg/ml rBSG and significant for MMP-3 at 10 mg/ml (FIG. 2). As a control for the potential effects of lipopolysaccharide (LPS) contamination of the rBSG protein on MMP expression, HESCs were treated with the amounts of LPS equal to that found in the rBSG treatments. The LPS treatments did not stimulate expression of MMPs.

To identify the receptors responsible for rBSG binding, the rBSG protein was used as an affinity purification reagent in combination with the heterotrifunctional cross-linking agent Sulfo-SBED. Sulfo-SBED possesses an NHS-ester group for labeling of rBSG, an aryl azide group for UV-light cross-linking of cell surface proteins to the rBSG ligand, and a biotin group for affinity purification of cross-linked protein complexes. A cleavable disulfide bond in the NHS-ester arm of Sulfo-SBED allows for the release of the crosslinker from the rBSG. Preliminary experiments to determine the amount of SBED-conjugated rBSG required for cell labeling indicated that the use of 50 mg/ml of rBSG for 10 minutes at 37° C. was sufficient to label the intact uterine fibroblasts, and all subsequent work employed these conditions for cell labeling.

Figure 3:
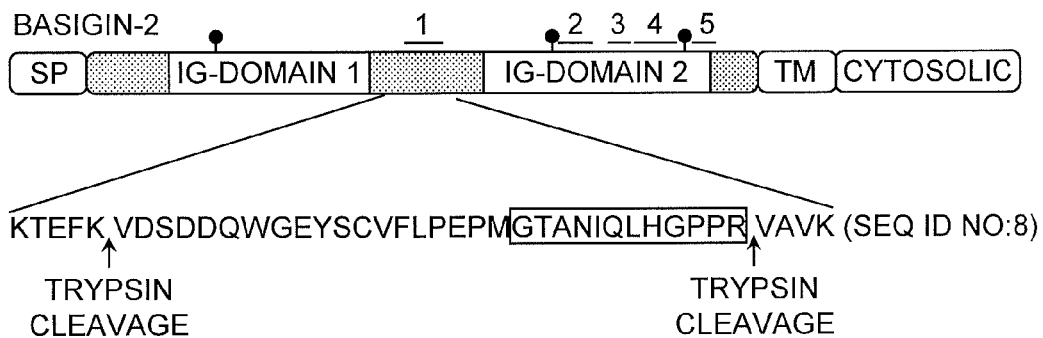
FIG. 3 shows MALDI MS/MS sequence analysis of the 25 kDa protein identified as basigin-3. Amino acid sequences of the tryptic peptides from the purified protein are shown. While the peptides align with the basigin-2 sequence, the 1260 Da peptide (Gly-Thr-Ala-Asn-Ile-Gln-Leu-His-Gly-Pro-Pro-Arg; SEQ ID NO:3) could not have been generated as a tryptic peptide of basigin-2. The mass of basigin-2 peptide that contains this 1260 Da peptide sequence (boxed) is predicted to be 7026 Da. Therefore, probability-based scoring obtained using the Mascot search engine indicated that the sequenced protein best matched the translated mRNA sequence for human basigin-3 (Accession No. gi|138372921).

Streptavidin immunoblotting of monomeric avidin-purified protein complexes identified several biotinylated proteins including two major bands at 25 kDa and ~50 kDa as well as three other less abundant proteins at 30, 100 and 120 kDa. The 25 kDa biotinylated protein, which was clearly visible by COOMASSIE staining, was subjected to tryptic digestion and MALDI MS/MS protein identification. The peptide sequences were compared to the non-redundant NCBI database using Mascot (Perkins, et al. (1999) Electrophoresis 20(18):3551-3567), and the results indicated that the peptides aligned with the human basigin-2 sequence (FIG. 3). However, peptide-1 (Gly-Thr-Ala-Asn-Ile-Gln-Leu-His-Gly-Pro-Pro-Arg; SEQ ID NO:3) could not have been generated by tryptic digestion of human basigin-2 (FIG. 3, bottom panel). Probability-based scoring using Mascot indicated that the peptide-1 sequence best matched the translated mRNA sequence for a novel human basigin isoform named basigin-3 (RefSeq Accession No. gi|138372921). While the mRNA sequence for basigin-3 (RefSeq Accession No. NM_198590) and another closely related isoform, basigin-4 (RefSeq Accession No. NM_198591) have been annotated within the RefSeq database, no published reports have described these molecules.

Figure 4:
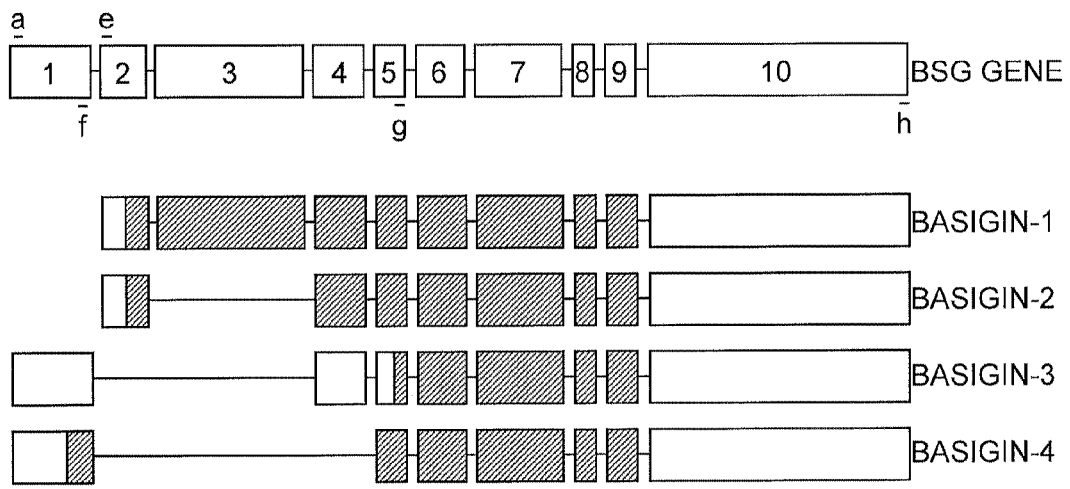
FIG. 4 shows intron-exon mapping of the human basigin gene sequence with the four mRNA sequences for human basigin using the program SPIDEY. The ten exons of the human basigin gene are shown at the top and the primers used in the study are indicated by lower case letters (a-e are sense primers, f-h are antisense primers). The filled boxes correspond to the predicted open reading frames, and the open boxes correspond to untranslated regions of the transcripts.

The nucleotide sequences of basigin-3 and basigin-4 were compared to existing basigin sequences using the program SPIDEY. Mapping of the intron-exon boundaries identified a 255 bp exon sequence that is 958 bp upstream of the previously identified first exon of basigin. This exon is predicted to be expressed only by the basigin-3 and basigin-4 isoforms (FIG. 4) and indicates that the human basigin gene is composed of 10 exons within human chromosome 19 covering 12.17 Kb (RefSeq Accession No. NC_000019.8). Northern analysis for basigin-3 and basigin-4 using the first exon sequence as a probe did not detect any specific transcripts in uterine fibroblasts, nor in polyA+ RNA blots from 18 human tissues. Therefore, reverse transcription PCR (RT-PCR) was performed using oligonucleotide primers corresponding to sequences within exons 1, 2, 5 and 10 of the basigin gene. The predicted size (in base pairs) of the resulting amplicons is listed in Table 2.

TABLE 2

| Primer Pairs | Basigin-1 | Basigin-2 | Basigin-3 | Basigin-4 |
| --- | --- | --- | --- | --- |
| a-f | — | — | 231 | 231 |
| a-g | — | — | 454 | 298 |
| e-g | 658 | 310 | — | — |
| a-h | — | — | 1745 | 1588 |
| e-h | 1949 | 1601 | — | — |

Amplification with primers specific to basigin-1 and basigin-2 (primers e, g) detected only the basigin-2 transcripts in the cell types tested. Amplification with primers specific to basigin-3 and basigin-4 (primers a, g) demonstrated the presence of both transcripts in the cell types tested. Quantitation of the relative transcript levels within each of the four cell lines was performed by densitometry using the ImageJ program. Following normalization for the amount of the PCR product loaded per lane, it was estimated that basigin-3 transcript levels were less than 3% of the basigin-2 levels in carcinoma cells, and less than 1% of basigin-2 levels in fibroblasts. To confirm the identity of the amplified cDNAs, the PCR products were subcloned and sequenced. With the exception of a single nucleotide polymorphism in the basigin-3 from CCL-2 cells, the amplified sequences were identical to the existing RefSeq basigin sequences. Alignment of the conceptually translated sequences for all four basigin isoforms (FIG. 5) demonstrated that they share a conserved core sequence (exon 5 through exon 10), and differ only in the extent of extracellular domain being expressed. One exception to this is the predicted 11 amino acid sequence at the amino terminus of basigin-4 (Met-Lys-Gln-Ser-Asp-Ala-Ser-Pro-Gln-Glu-Arg; SEQ ID NO:21) that is unique to this isoform.

Figure 6A:
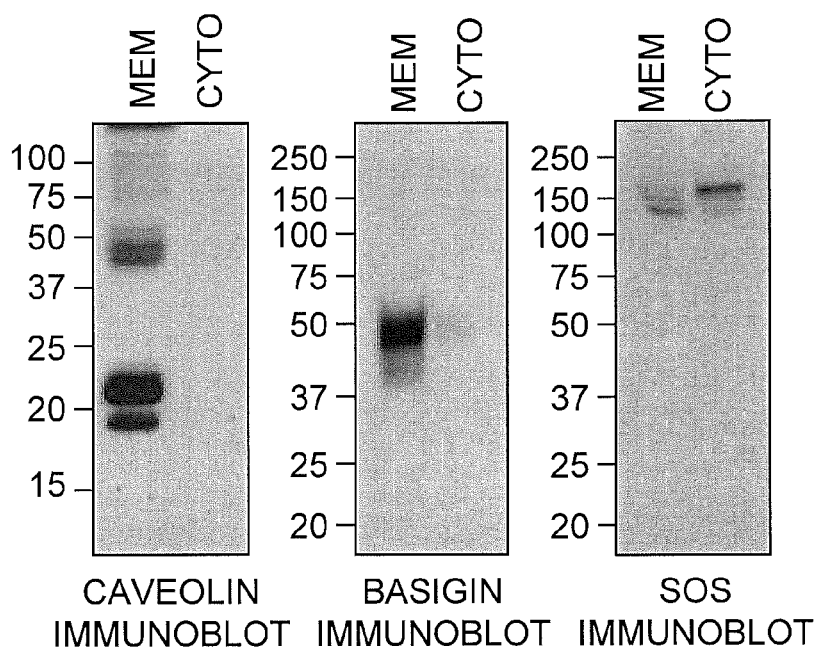
Figure 6B:
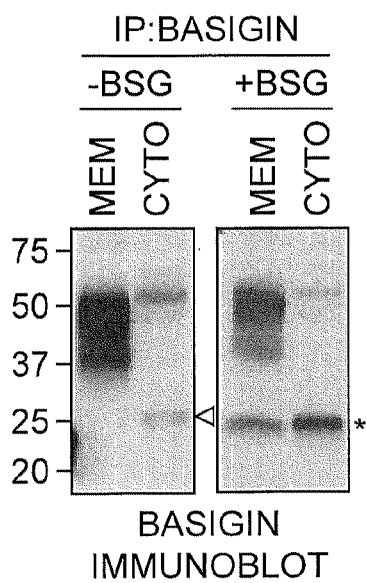
In FIG. 6B, unlabeled HESC fractions (left panel) were immunoprecipitated with the basigin mAb P2C2 and immunoblotted with the R & D anti-EMMPRIN pAb. Note the presence of the 25-kDa basigin-3 protein exclusively in the cytosolic sample from unlabeled cells (arrowhead). Basigin immunoprecipitations (IP) from labeled cells (right panel) shows that the rBSG protein was present in both the membrane and cytosolic fractions (asterisk). The basigin-3 band could not be distinguished from the rBSG band in the cytosolic fraction because of the similarities in the size of both proteins.
Figure 6C:
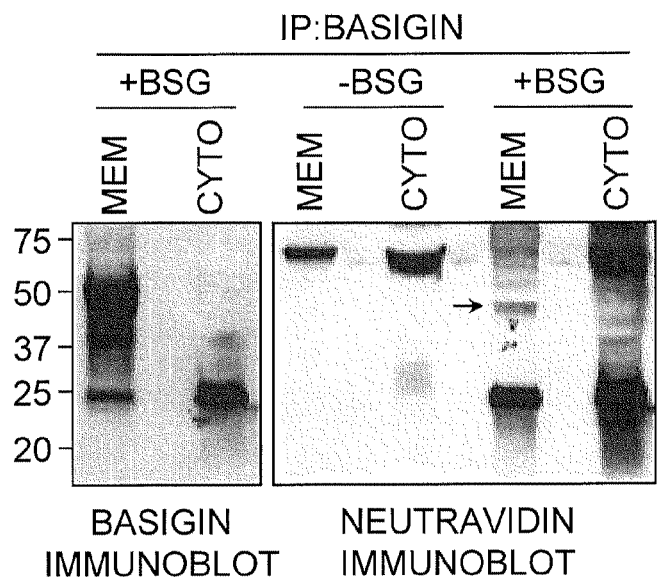
In FIG. 6C, neutravidin immunoblotting shows that basigin-2 in the membrane is biotinylated in response to rBSG-SBED treatment. Basigin proteins were immunoprecipitated from HESC fractions using the mAb P2C2 and immunoblotted with either the EMMPRIN pAb (left panel) or neutravidin-HRP (right panel). A portion of the basigin-2 protein from the membrane is biotinylated (arrow).
Figures 7A, 7B, 7C, 7D:
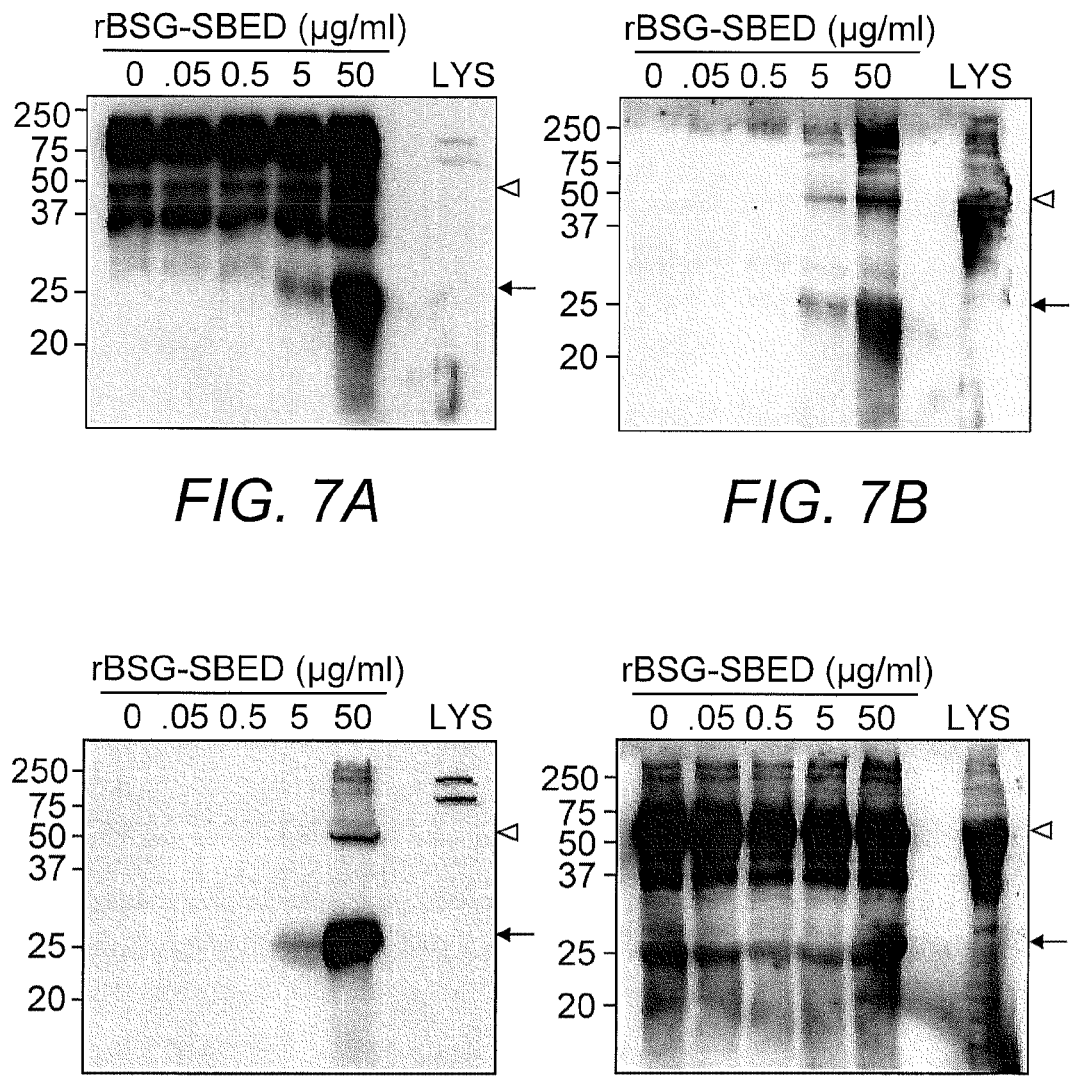

The proteomic data herein demonstrated the association of rBSG with basigin-3 indicating that these proteins interacted during the 10 minute labeling period prior to UV treatment of the cells. However, basigin-3 does not possess a consensus signal peptide sequence normally required for membrane localization. In order to explain how the basigin-3 protein might interact with rBSG, protein localization studies were performed. Cells were separated into membrane and cytoplasmic fractions, and used for immunoblot analysis. Control experiments using antibodies specific for the membrane protein caveolin-1 and the cytoplasmic protein SOS labeled the expected fractions (FIG. 6A). Similarly, basigin immunoblot analysis detected basigin-2 in the membrane fraction, but did not detect the 25 kDa basigin-3 protein in either fraction (FIG. 6A, middle panel). RT-PCR data suggested that basigin-3 might be expressed at levels too low to be detected by immunoblot analysis of cell lysates. In order to detect low-abundance isoforms, basigin proteins were immunoprecipitated from HESC fractions and then immunoblotted. The results showed that in the absence of rBSG labeling, the 25 kDa protein corresponding to basigin-3 was detected exclusively in the cytoplasmic fraction (FIG. 6B, arrowhead in left panel). Repeating this procedure using fractions from labeled cells revealed a significant increase in the band(s) at ~25 kDa in both the membrane and cytoplasmic fractions. Since the relative molecular weight of rBSG (23 kDa) was nearly the same as that for basigin-3, the increase in basigin immunoreactivity at 23-25 kDa in both the membrane and cytoplasmic fractions from labeled cells (FIG. 6B, right panel) indicates that this increase was due to the presence of rBSG in both fractions. This result indicates that rBSG associates with an unknown membrane receptor prior to being internalized into the cell. It has been suggested that basigin-2 can function as the membrane receptor for soluble basigin protein, but attempts to directly test this hypothesis have not demonstrated this ability (Hanna, et al. (2003) supra; Yoshida et al. (2000) supra). This aspect was examined by repeating the basigin immunoprecipitations from labeled HESC fractions, followed by immunoblot analysis with NEUTRAVIDIN-HRP to detect the transfer of the biotin label from the SEED-labeled rBSG to basigin-2 in the membrane fraction. The results revealed that a 50 kDa basigin protein in the membrane fraction was biotinylated only following treatment of uterine fibroblasts with SBED-labeled rBSG (FIG. 7C). Confirmation of the interaction between soluble rBSG and basigin-2 was demonstrated by repeating the label transfer experiment using the cervical adenocarcinoma cell line CCL-2. Reciprocal precipitations from total cell lysates using the basigin monoclonal antibody and NEUTRAVIDIN beads were performed, and the precipitated proteins immunoblotted with basigin polyclonal antibody and Streptavidin-HRP (FIG. 7). The results showed specific labeling of the 50 kDa basigin-2 protein as well as the 25 kDa basigin-3 protein.

To test the necessity for basigin-2 in rBSG-mediated cell signaling events, small interfering RNAs (siRNAs) were employed to knock down basigin-2 protein expression in HESCs. These siRNAs were: sense strand, 5'-GCU ACA CAU UGA GAA CCU Gtt-3' (SEQ ID NO:22); and antisense strand, 5'-CAG GUU CUC AAU GUG UAG Ctc-3' (SEQ ID NO:23). Cells were transfected with either negative control or basigin siRNAs for 48 hours, and treated with rBSG to measure changes in ERK1/2 phosphorylation. Treatment with rBSG activated the ERK1/2 signaling pathway in the negative control siRNA experiments, with maximal ERK phosphorylation occurring within 10-15 minutes of rBSG addition. Despite a nearly quantitative knockdown of basigin protein in the basigin siRNA transfected cells, rBSG was still capable of stimulating ERK phosphorylation, but to a lesser extent. Treatment of the HESCs with recombinant human EGF (rhEGF) stimulated the ERK signaling pathway regardless of the presence of endogenous basigin protein.

Example 3

Elimination of Targeted Cells with an Anti-BSG Antibody Linked to Saporin

Figure 8:
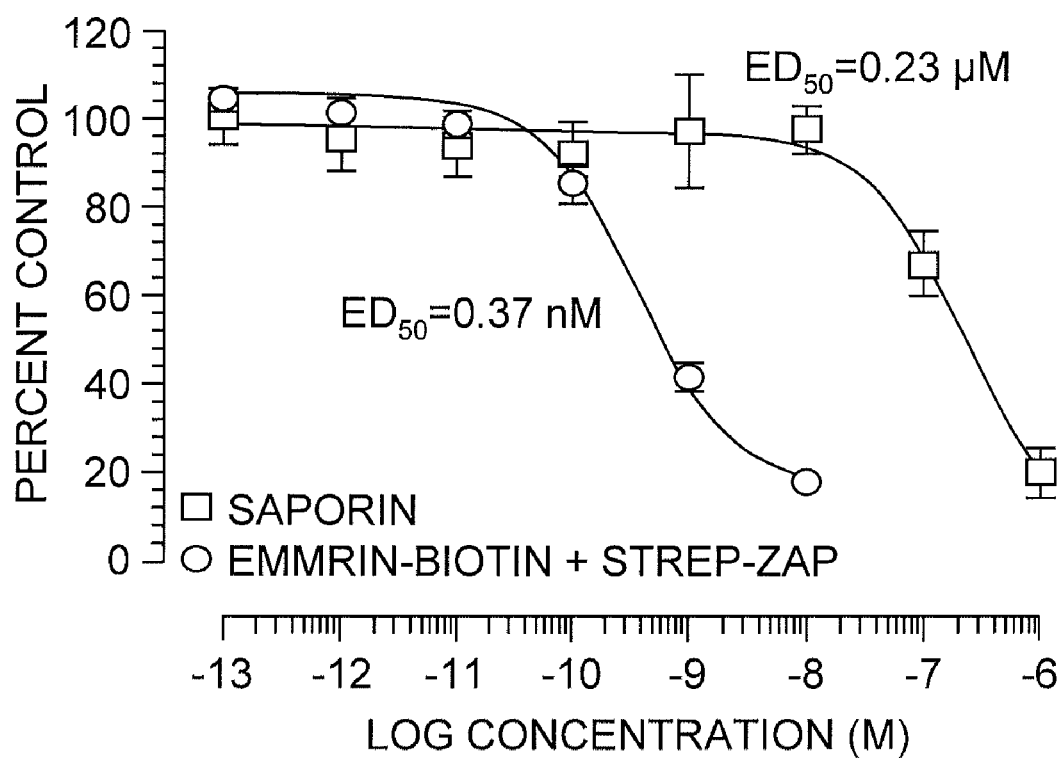
FIG. 8 shows the effects of a Streptavidin-ZAP/Biotinylated-anti-Emmprin-saporin mixture on target cells. HeLa cells, a CCL-2 cervical cancer cell line, were plated at 1000 cells/90 µl/well in a 96-well plate and incubated overnight. Streptavidin-ZAP was premixed with Biotinylated-anti-Emmprin-saporin (P2C2-1-D11) in equimolar concentrations. Saporin alone or the Streptavidin-ZAP+Biotinylated-Emmprin-saporin mixture were then added in 10-µl volumes and the plates were incubated 72 hours. PMS/MTS developing reagent was then added and the plate was incubated for 20 minutes and read at 490 nm in a plate reader. Data analysis was done by PRISM (GraphPad). The Streptavidin-ZAP+Biotinylated-anti-Emmprin-saporin eliminated up to 82% of the target population. Saporin by itself had little effect on the cancer cells.

Streptavidin-ZAP available from Advanced Targeting Systems (San Diego, Calif.) is a tool that allows evaluation of targeted toxin efficacy using any molecule that can be biotinylated as a targeting agent. To employ the Streptavidin-ZAP, the anti-BSG antibody was first linked to saporin and then biotinylated. The biotinylated molecule and Streptavidin-ZAP were then combined in equimolar concentrations so that the streptavidin and biotin formed a complex. The Streptavidin-ZAP/Biotinylated-anti-basigin antibody-saporin complex was then added to HeLa cells, with saporin alone as a control, and internalization and release of the saporin from the streptavidin was determined by cell death. As shown in FIG. 8, the Streptavidin-ZAP+Biotinylated-anti-BSG/EMMPRIN-saporin mixture eliminated up to 82% of the target population.

What is claimed is:

1. A composition for facilitating the internalization of a therapeutic agent into a cell, comprising a delivery moiety operably linked to a therapeutic agent, wherein the delivery moiety is the extracellular domain of basigin-2, wherein the basigin-2 is not glycosylated; and the therapeutic agent comprises an anti-inflammatory protein, anti-viral, anti-parasitic, anti-bacterial, endocrine drug, metabolic drug, mitotoxin, chemotherapy drug, or siRNA.

2. A composition for facilitating the internalization of a therapeutic agent into a cell, comprising a delivery moiety operably linked to a therapeutic agent, wherein the delivery moiety is the extracellular domain of basigin-2, wherein the extracellular domain of basigin-2 comprises SEQ ID NO:13; and the therapeutic agent comprises an anti-inflammatory protein, anti-viral, anti-parasitic, anti-bacterial, endocrine drug, metabolic drug, mitotoxin, chemotherapy drug, or siRNA.

* * * * *

SEQUENCE LISTING

```
<160> NUMBER OF SEQ ID NOS: 23

<210> SEQ ID NO 1
<211> LENGTH: 8
<212> TYPE: PRT
<213> ORGANISM: Artificial sequence
<220> FEATURE:
<223> OTHER INFORMATION: Synthetic peptide

<400> SEQUENCE: 1

Trp Ser His Pro Gln Phe Glu Lys
1               5
```

```
<210> SEQ ID NO 2
<211> LENGTH: 6
<212> TYPE: PRT
<213> ORGANISM: Artificial sequence
<220> FEATURE:
<223> OTHER INFORMATION: Synthetic peptide

<400> SEQUENCE: 2

His His His His His His
1               5

<210> SEQ ID NO 3
<211> LENGTH: 12
<212> TYPE: PRT
<213> ORGANISM: Artificial sequence
<220> FEATURE:
<223> OTHER INFORMATION: Synthetic peptide

<400> SEQUENCE: 3

Gly Thr Ala Asn Ile Gln Leu His Gly Pro Pro Arg
1               5                   10

<210> SEQ ID NO 4
<211> LENGTH: 14
<212> TYPE: PRT
<213> ORGANISM: Artificial sequence
<220> FEATURE:
<223> OTHER INFORMATION: Synthetic peptide

<400> SEQUENCE: 4

Ser Glu Ser Val Pro Pro Val Thr Asp Trp Ala Trp Tyr Lys
1               5                   10

<210> SEQ ID NO 5
<211> LENGTH: 9
<212> TYPE: PRT
<213> ORGANISM: Artificial sequence
<220> FEATURE:
<223> OTHER INFORMATION: Synthetic peptide

<400> SEQUENCE: 5

Phe Phe Val Ser Ser Ser Gln Gly Arg
1               5

<210> SEQ ID NO 6
<211> LENGTH: 18
<212> TYPE: PRT
<213> ORGANISM: Artificial sequence
<220> FEATURE:
<223> OTHER INFORMATION: Synthetic peptide

<400> SEQUENCE: 6

Ser Glu Leu His Ile Glu Asn Leu Asn Met Glu Ala Asp Pro Gly Gln
1               5                   10                  15

Tyr Arg

<210> SEQ ID NO 7
<211> LENGTH: 10
<212> TYPE: PRT
<213> ORGANISM: Artificial sequence
<220> FEATURE:
<223> OTHER INFORMATION: Synthetic peptide

<400> SEQUENCE: 7

Gly Ser Asp Gln Ala Ile Ile Thr Leu Arg
1               5                   10
```

```
<210> SEQ ID NO 8
<211> LENGTH: 40
<212> TYPE: PRT
<213> ORGANISM: Artificial sequence
<220> FEATURE:
<223> OTHER INFORMATION: Synthetic peptide

<400> SEQUENCE: 8

Lys Thr Glu Phe Lys Val Asp Ser Asp Asp Gln Trp Gly Glu Tyr Ser
1               5                   10                  15

Cys Val Phe Leu Pro Glu Pro Met Gly Thr Ala Asn Ile Gln Leu His
                20                  25                  30

Gly Pro Pro Arg Val Ala Val Lys
            35                  40

<210> SEQ ID NO 9
<211> LENGTH: 385
<212> TYPE: PRT
<213> ORGANISM: Homo sapiens

<400> SEQUENCE: 9

Met Ala Ala Ala Leu Phe Val Leu Leu Gly Phe Ala Leu Leu Gly Thr
1               5                   10                  15

His Gly Ala Ser Gly Ala Ala Gly Phe Val Gln Ala Pro Leu Ser Gln
                20                  25                  30

Gln Arg Trp Val Gly Gly Ser Glu Leu His Cys Glu Ala Val Gly
            35                  40                  45

Ser Pro Val Pro Glu Ile Gln Trp Trp Phe Glu Gly Gln Gly Pro Asn
    50                  55                  60

Asp Thr Cys Ser Gln Leu Trp Asp Gly Ala Arg Leu Asp Arg Val His
65                  70                  75                  80

Ile His Ala Thr Tyr His Gln His Ala Ala Ser Thr Ile Ser Ile Asp
                85                  90                  95

Thr Leu Val Glu Glu Asp Thr Gly Thr Tyr Glu Cys Arg Ala Ser Asn
                100                 105                 110

Asp Pro Asp Arg Asn His Leu Thr Arg Ala Pro Arg Val Lys Trp Val
            115                 120                 125

Arg Ala Gln Ala Val Val Leu Val Leu Glu Pro Gly Thr Val Phe Thr
        130                 135                 140

Thr Val Glu Asp Leu Gly Ser Lys Ile Leu Leu Thr Cys Ser Leu Asn
145                 150                 155                 160

Asp Ser Ala Thr Glu Val Thr Gly His Arg Trp Leu Lys Gly Gly Val
                165                 170                 175

Val Leu Lys Glu Asp Ala Leu Pro Gly Gln Lys Thr Glu Phe Lys Val
            180                 185                 190

Asp Ser Asp Asp Gln Trp Gly Glu Tyr Ser Cys Val Phe Leu Pro Glu
        195                 200                 205

Pro Met Gly Thr Ala Asn Ile Gln Leu His Gly Pro Pro Arg Val Lys
    210                 215                 220

Ala Val Lys Ser Ser Glu His Ile Asn Glu Gly Glu Thr Ala Met Leu
225                 230                 235                 240

Val Cys Lys Ser Glu Ser Val Pro Pro Val Thr Asp Trp Ala Trp Tyr
                245                 250                 255

Lys Ile Thr Asp Ser Glu Asp Lys Ala Leu Met Asn Gly Ser Glu Ser
            260                 265                 270

Arg Phe Phe Val Ser Ser Ser Gln Gly Arg Ser Glu Leu His Ile Glu
        275                 280                 285
```

Asn Leu Asn Met Glu Ala Asp Pro Gly Gln Tyr Arg Cys Asn Gly Thr
290                 295                 300

Ser Ser Lys Gly Ser Asp Gln Ala Ile Ile Thr Leu Arg Val Arg Ser
305                 310                 315                 320

His Leu Ala Ala Leu Trp Pro Phe Leu Gly Ile Val Ala Glu Val Leu
            325                 330                 335

Val Leu Val Thr Ile Ile Phe Ile Tyr Glu Lys Arg Arg Lys Pro Glu
            340                 345                 350

Asp Val Leu Asp Asp Asp Ala Gly Ser Ala Pro Leu Lys Ser Ser
            355                 360             365

Gly Gln His Gln Asn Asp Lys Gly Lys Asn Val Arg Gln Arg Asn Ser
    370                 375                 380

Ser
385

<210> SEQ ID NO 10
<211> LENGTH: 269
<212> TYPE: PRT
<213> ORGANISM: Homo sapiens

<400> SEQUENCE: 10

Met Ala Ala Ala Leu Phe Val Leu Leu Gly Phe Ala Leu Leu Gly Thr
1               5                   10                  15

His Gly Ala Ser Gly Ala Ala Gly Thr Val Phe Thr Thr Val Glu Asp
                20                  25                  30

Leu Gly Ser Lys Ile Leu Leu Thr Cys Ser Leu Asn Asp Ser Ala Thr
            35                  40                  45

Glu Val Thr Gly His Arg Trp Leu Lys Gly Gly Val Val Leu Lys Glu
    50                  55                  60

Asp Ala Leu Pro Gly Gln Lys Thr Glu Phe Lys Val Asp Ser Asp Asp
65                  70                  75                  80

Gln Trp Gly Glu Tyr Ser Cys Val Phe Leu Pro Glu Pro Met Gly Thr
                85                  90                  95

Ala Asn Ile Gln Leu His Gly Pro Pro Arg Val Lys Ala Val Lys Ser
            100                 105                 110

Ser Glu His Ile Asn Glu Gly Glu Thr Ala Met Leu Val Cys Lys Ser
        115                 120                 125

Glu Ser Val Pro Pro Val Thr Asp Trp Ala Trp Tyr Lys Ile Thr Asp
130                 135                 140

Ser Glu Asp Lys Ala Leu Met Asn Gly Ser Glu Ser Arg Phe Phe Val
145                 150                 155                 160

Ser Ser Ser Gln Gly Arg Ser Glu Leu His Ile Glu Asn Leu Asn Met
                165                 170                 175

Glu Ala Asp Pro Gly Gln Tyr Arg Cys Asn Gly Thr Ser Ser Lys Gly
            180                 185                 190

Ser Asp Gln Ala Ile Ile Thr Leu Arg Val Arg Ser His Leu Ala Ala
        195                 200                 205

Leu Trp Pro Phe Leu Gly Ile Val Ala Glu Val Leu Val Leu Val Thr
210                 215                 220

Ile Ile Phe Ile Tyr Glu Lys Arg Arg Lys Pro Glu Asp Val Leu Asp
225                 230                 235                 240

Asp Asp Ala Gly Ser Ala Pro Leu Lys Ser Ser Gly Gln His Gln
                245                 250                 255

Asn Asp Lys Gly Lys Asn Val Arg Gln Arg Asn Ser Ser
            260                 265

-continued

```
<210> SEQ ID NO 11
<211> LENGTH: 176
<212> TYPE: PRT
<213> ORGANISM: Homo sapiens

<400> SEQUENCE: 11

Met Gly Thr Ala Asn Ile Gln Leu His Gly Pro Pro Arg Val Lys Ala
1               5                   10                  15

Val Lys Ser Ser Glu His Ile Asn Glu Gly Glu Thr Ala Met Leu Val
            20                  25                  30

Cys Lys Ser Glu Ser Val Pro Pro Val Thr Asp Trp Ala Trp Tyr Lys
        35                  40                  45

Ile Thr Asp Ser Glu Asp Lys Ala Leu Met Asn Gly Ser Glu Ser Arg
    50                  55                  60

Phe Phe Val Ser Ser Gln Gly Arg Ser Glu Leu His Ile Glu Asn
65                  70                  75                  80

Leu Asn Met Glu Ala Asp Pro Gly Gln Tyr Arg Cys Asn Gly Thr Ser
                85                  90                  95

Ser Lys Gly Ser Asp Gln Ala Ile Ile Thr Leu Arg Val Arg Ser His
            100                 105                 110

Leu Ala Ala Leu Trp Pro Phe Leu Gly Ile Val Ala Glu Val Leu Val
        115                 120                 125

Leu Val Thr Ile Ile Phe Ile Tyr Glu Lys Arg Arg Lys Pro Glu Asp
    130                 135                 140

Val Leu Asp Asp Asp Ala Gly Ser Ala Pro Leu Lys Ser Ser Gly
145                 150                 155                 160

Gln His Gln Asn Asp Lys Gly Lys Asn Val Arg Gln Arg Asn Ser Ser
                165                 170                 175

<210> SEQ ID NO 12
<211> LENGTH: 204
<212> TYPE: PRT
<213> ORGANISM: Homo sapiens

<400> SEQUENCE: 12

Met Lys Gln Ser Asp Ala Ser Pro Gln Glu Val Asp Ser Asp Gln
1               5                   10                  15

Trp Gly Glu Tyr Ser Cys Val Phe Leu Pro Glu Pro Met Gly Thr Ala
            20                  25                  30

Asn Ile Gln Leu His Gly Pro Pro Arg Val Lys Ala Val Lys Ser Ser
        35                  40                  45

Glu His Ile Asn Glu Gly Glu Thr Ala Met Leu Val Cys Lys Ser Glu
    50                  55                  60

Ser Val Pro Pro Val Thr Asp Trp Ala Trp Tyr Lys Ile Thr Asp Ser
65                  70                  75                  80

Glu Asp Lys Ala Leu Met Asn Gly Ser Glu Ser Arg Phe Phe Val Ser
                85                  90                  95

Ser Ser Gln Gly Arg Ser Glu Leu His Ile Glu Asn Leu Asn Met Glu
            100                 105                 110

Ala Asp Pro Gly Gln Tyr Arg Cys Asn Gly Thr Ser Ser Lys Gly Ser
        115                 120                 125

Asp Gln Ala Ile Ile Thr Leu Arg Val Arg Ser His Leu Ala Ala Leu
    130                 135                 140

Trp Pro Phe Leu Gly Ile Val Ala Glu Val Leu Val Leu Val Thr Ile
145                 150                 155                 160

Ile Phe Ile Tyr Glu Lys Arg Arg Lys Pro Glu Asp Val Leu Asp Asp
                165                 170                 175
```

Asp Asp Ala Gly Ser Ala Pro Leu Lys Ser Ser Gly Gln His Gln Asn
            180                 185                 190

Asp Lys Gly Lys Asn Val Arg Gln Arg Asn Ser Ser
        195                 200

<210> SEQ ID NO 13
<211> LENGTH: 183
<212> TYPE: PRT
<213> ORGANISM: Artificial sequence
<220> FEATURE:
<223> OTHER INFORMATION: Synthetic peptide

<400> SEQUENCE: 13

Gly Thr Val Phe Thr Val Glu Asp Leu Gly Ser Lys Ile Leu Leu
1               5                   10                  15

Thr Cys Ser Leu Asn Asp Ser Ala Thr Glu Val Thr Gly His Arg Trp
            20                  25                  30

Leu Lys Gly Gly Val Val Leu Lys Glu Asp Ala Leu Pro Gly Gln Lys
        35                  40                  45

Thr Glu Phe Lys Val Asp Ser Asp Asp Gln Trp Gly Glu Tyr Ser Cys
    50                  55                  60

Val Phe Leu Pro Glu Pro Met Gly Thr Ala Asn Ile Gln Leu His Gly
65                  70                  75                  80

Pro Pro Arg Val Lys Ala Val Lys Ser Ser Glu His Ile Asn Glu Gly
                85                  90                  95

Glu Thr Ala Met Leu Val Cys Lys Ser Glu Ser Val Pro Pro Val Thr
            100                 105                 110

Asp Trp Ala Trp Tyr Lys Ile Thr Asp Ser Glu Asp Lys Ala Leu Met
        115                 120                 125

Asn Gly Ser Glu Ser Arg Phe Phe Val Ser Ser Ser Gln Gly Arg Ser
    130                 135                 140

Glu Leu His Ile Glu Asn Leu Asn Met Glu Ala Asp Pro Gly Gln Tyr
145                 150                 155                 160

Arg Cys Asn Gly Thr Ser Ser Lys Gly Ser Asp Gln Ala Ile Ile Thr
                165                 170                 175

Leu Arg Val Arg Ser His Leu
            180

<210> SEQ ID NO 14
<211> LENGTH: 39
<212> TYPE: DNA
<213> ORGANISM: Artificial sequence
<220> FEATURE:
<223> OTHER INFORMATION: Synthetic oligonucleotide

<400> SEQUENCE: 14
atggtaggtc tcagcgccgc cggcacagtc ttcactacc                             39

<210> SEQ ID NO 15
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 15
atggtaggtc tcaggcccag gtggctgcgc acgcgg                                36

```
<210> SEQ ID NO 16
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 16
cggcttagtc tgcggtcc                                                  18

<210> SEQ ID NO 17
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 17
gcggttggag gttgtaggac                                                20

<210> SEQ ID NO 18
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 18
tccgactgct tcattgtggg                                                20

<210> SEQ ID NO 19
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 19
gggaggaaga cgcaggagta                                                20

<210> SEQ ID NO 20
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 20 tttttttgagg gtggaggtgg                                               20

<210> SEQ ID NO 21
<211> LENGTH: 11
<212> TYPE: PRT
<213> ORGANISM: Artificial sequence
<220> FEATURE:
<223> OTHER INFORMATION: Synthetic peptide

<400> SEQUENCE: 21

Met Lys Gln Ser Asp Ala Ser Pro Gln Glu Arg
1               5                   10

<210> SEQ ID NO 22
<211> LENGTH: 21
<212> TYPE: DNA
<213> ORGANISM: Artificial sequence
<220> FEATURE:
<223> OTHER INFORMATION: Synthetic oligonucleotide
```

```
-continued

<400> SEQUENCE: 22
gcuacacauu gagaaccugt t                                              21

<210> SEQ ID NO 23
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 23
cagguucuca auguguagct c                                              21
```